United States Patent [19]

Ebling et al.

[11] Patent Number: 4,592,749
[45] Date of Patent: Jun. 3, 1986

[54] CATHETER SYSTEM

[75] Inventors: Wendell V. Ebling, Placentia, Calif.; James H. DeVries, Grand Rapids, Mich.

[73] Assignee: Gish Biomedical, Inc., Santa Ana, Calif.

[21] Appl. No.: 623,110

[22] Filed: Jun. 22, 1984

[51] Int. Cl.[4] .............................................. A61M 25/00
[52] U.S. Cl. ..................................... 604/283; 285/239
[58] Field of Search ................. 604/283, 285; 285/239, 285/242, 255

[56] References Cited
U.S. PATENT DOCUMENTS

| | | | |
|---|---|---|---|
| 585,014 | 6/1897 | Wenzel et al. | 285/239 |
| 1,994,784 | 3/1935 | Porzel | 285/239 |
| 4,049,034 | 9/1977 | Vcelka et al. | 285/242 X |
| 4,484,922 | 11/1984 | Rosenwald | 604/893 |
| 4,511,163 | 4/1985 | Harris et al. | 604/283 |

FOREIGN PATENT DOCUMENTS 1003914  3/1957  Fed. Rep. of Germany ...... 604/895

Primary Examiner—Stephen C. Pellegrino
Attorney, Agent, or Firm—Robert J. Schaap

[57] ABSTRACT

A catheter system in which a silicone rubber catheter tube may be secured to the cylindrically shaped relatively smooth stem of a rigid plastic fitting. A rigid plastic sleeve is adapted to extend over the tube when the latter is fitted onto the stem of the fitting to create a fluid tight seal between the tubing and the fitting. In another embodiment, a boot may first be disposed over a portion of the silicone rubber tubing and then extended over the connection of the rigid sleeve and rubber tubing and plastic fitting. In still a further embodiment a combination boot-sleeve may be employed and sealed to a fitting by means of an ultrasonic weld.

14 Claims, 11 Drawing Figures

CATHETER SYSTEM

BACKGROUND OF THE INVENTION

1. Field of the Invention

This invention relates in general to certain new and useful improvements in catheter systems, and more particularly, to a method and assembly for securing a flexible and somewhat stretchable silicone rubber tube to a plastic fitting.

2. Brief Description of the Prior Art

Intraveneous catheter systems are widely used in surgical and post-surgical procedures and particularly in many hospital environments. For example, central venal access catheters are commonly employed in cardiac post-surgical procedures. One end of the catheter tube is introduced into the body venal system through an incision formed in the body, and the other end which remains external to the body, is provided with a fitting and a removeable cap on the fitting. In this way, the cap can be removed for connection to a source of intraveneously injected fluid.

One of the preferred tubings used in the catheter system is a silicone rubber tube. This tube has been selected due to its human tissue compatability, and resiliency and flexibility as well as the fact that it is capable of being effectively used in sterile environments. However, it has also been recognized that one of the principal problems in the use of this tubing is the securement of the tubing in a fluid tight condition to a rigid plastic fitting such as a polyethylene or polyvinyl or polypropylene fitting. A fluid tight seal between the fitting or so-called "luer" and the tubing is essential in order to preclude leakage of any intraveneous fluid to be injected. The fluid tight seal is equally important to preclude the body cavity from being open to the external environment through an ineffective seal between the tubing and the fitting.

In order to obtain a relatively fluid tight seal, many prior art fittings have resorted to the use of so-called "barbs" e.g. spaced apart cylindrically shaped outwardly projecting ribs on the cylindrically shaped stem of the fitting. These ribs or barbs protrude beyond the stem surface to extend into and slightly deform the silicone rubber tube. It has been found, however, that these barbs do not necessarily provide a fluid tight seal and in many cases, after a short period of use, will tend to cut into the silicone rubber tubing and thereby ultimately lead to a fracture of the tubing.

In other attempts to obtain a fluid tight seal, sutures were used for wrapping about the rubber tubing as it extended over a stem on the fitting to thereby tightly compress the rubber tubing about the stem of the fitting, at least in the regions of the sutures. This wrapping technique in combination with adhesives has also been employed. This technique for adhering the rubber tubing to the plastic stem of the fitting results in cosmetically inferior joinder regions. Further, this technique results in a more costly seal and hence a more costly device due to ecessive labor time for wrapping the sutures. It has also been shown with silicone rubber that sharp sutures can cut into the silicone rubber after a period of time.

U.S. Pat. No. 1,723,273 to Irwin discloses a coupling member used for catheter tubes with a central hub containing a plurality of barbs to retain a tube inserted over the coupling member. A metallic locking collar having a tapered end is slid over the tube to hold it in place.

U.S. Pat. No. 626,210 to Deitz also shows a coupling member with only one barb on the end thereof and with a locking collar positioned interior to the barb. In this case, the locking collar extends only over a very small portion of the tube.

U.S. Pat. No. 161,492 to Dayton also discloses a hose joint which uses a single locking collar.

OBJECTS OF THE INVENTION

It is, therefore, one of the primary objects of the present invention to provide a connection system for use with catheter tubes which utilizes a smooth surface on a stem of a fitting and a smooth surfaced interior bore of a somewhat stretchable catheter tube along with a locking sleeve to form an essentially fluid tight seal therebetween.

It is another object of the present invention to provide a connection system of the type stated in which a boot is designed to extend over a locking sleeve which surrounds a connection of a catheter tube to a fitting to provide, not only an air tight seal, but a seal which precludes microbial intrusion and contamination.

It is a further object of the present invention to provide a connection system of the type stated which may be used with new assemblies of catheter tubes and luer or which may be used in a repair kit for connecting the broken ends of a catheter tube.

It is an additional object of the present invention to provide a connection system of the type stated which provides a positive mechanical lock between a silicone rubber tubing and a plastic luer fitting and which is relatively inexpensive to manufacture and highly effective in use.

With the above and other objects in view, our invention resides in the novel features of form, construction, arrangement, and combination of parts presently described and pointed out in the claims.

BRIEF SUMMARY OF THE DISCLOSURE

A system for connecting a catheter tube to a fitting with a fluid type seal. The system typically employs a flexible and somewhat stretchable catheter tube having an interior bore and preferably formed of a silicone rubber. In addition, a fitting having an elongate cylindrically shaped stem and having an outer surface consisting of a smooth outer surface is sized to fit within the bore of the silicone rubber catheter tube in a relatively fluid tight engagement therewith. The catheter tube is flexible and somewhat stretchable and has a relatively smooth interior bore.

A shoulder is formed on the stem and is adapted to be engaged by an end of the catheter tubing. The end of the tubing abuts against a flat surface of the shoulder. In addition, a relatively rigid sleeve is sized to fit over the portion of the catheter tube on the elongate stem and tightly engage the exterior surface of the tube and compress the same against the stem to insure a relatively tight fluid seal between this fitting and the tube. The sleeve also abuts the flat surface of the shoulder.

The invention also covers the connected catheter tube and fitting combination such that the tube is fitted over the stem of the catheter to completely abut against the shoulder on the enlarged stem, but not to extend over the shoulder, and the sleeve is fitted over the portion of the tube surrounding the stem.

In one embodiment of the invention, the tube is connected to a luer fitting of the type that has a cap capable of being disposed over one end of the fitting opposite the stem. In this way, the silicone rubber tubing is fitted in a relatively permanent engagement on a luer fitting supplied in a package for ultimate use in various surgical and therapeutic procedures.

In another embodiment, the system of the invention is used for repair of catheter tubing. In this case, the fitting comprises a second elongate cylindrically shaped stem wherein the outer surface also consists of a smooth outer surface having no substantial irregularities therein. A second shoulder is located at the end of the second elongate stem and an extension integrally connects the two stems. In this embodiment, a second relatively rigid sleeve is sized to extend over a second catheter tube on the second elongate stem and tightly engage the exterior surface of this tube and compress the same about the second stem. In this way, when a catheter tube is severed, it is possible to use the fitting and the assembly of the invention to connect another catheter tube portion to the severed one.

In each embodiment of the invention, a boot is sized to extend over the relatively rigid sleeve and a portion of the tube not covered by the sleeve, this boot is also capable of extending up to and engaging the shoulder on the fitting.

In still another embodiment of the invention, a combination of sleeve-boot which provides and performs the functions of both the boot and the sleeve is provided. In this embodiment, the sleeve-boot combination can be welded to the fitting, as for example, by ultrasonic welding. in this way, torsional forces will not cause a separation of the boot or the sleeve from the fitting and will also preclude severing of the catheter tube.

The invention also relates to a method of connecting an end of a silicone tube to a fitting to provide a fluid tight seal. The method generally comprises the overlying of a silicone rubber boot over a portion of a flexible and somewhat stretchable silicone rubber catheter tube. In addition, a relatively rigid sleeve is then next applied over a portion of the plastic tube nearer an end thereof than the boot. Thereafter, the method involves the inserting of the cylindrically shaped elongate stem of the fitting, with an outer surface consisting of a smooth outer surface with no substantial irregularities therein, into the bore of a flexible and somewhat stretchable silicone rubber catheter tube. This end of the tube is pushed along the stem until the end is in abutting engagement with an outwardly flaring shoulder at the end of the stem. The sleeve is pushed over the portion of the tube on the stem of the fitting until the sleeve abuts the shoulder on the fitting and tightly engages that portion of the tube and presses the same against the fitting. Finally, the method comprises pushing the boot over the sleeve until one end of the boot extends beyond the annular edge of the shoulder and the boot also extends over the entire sleeve and a portion of the tube beyond the sleeve.

The method may also utilize the inserting of another catheter tube over a second stem on the fitting much in the same manner as the first stem is fitted and secured with a sleeve and a boot.

In a more preferred embodiment of the invention, the boot is first introduced over the exterior surface of a relatively rigid mounting tube and one end of the catheter tube is inserted into and pulled through the mounting tube. Thereafter, the boot is slipped off of the mounting tube and onto the catheter tube.

This invention possesses many other advantages and has other purposes which may be made more clearly apparent from a consideration of forms in which it may be embodied. These forms are shown in the drawings accompanying and forming part of the present specification. They will now be described in detail, for the purpose of illustrating the general principles of the invention; but it is to be understood that such detailed descriptions are not to be taken in a limiting sense.

BRIEF DESCRIPTIONS OF THE DRAWINGS

Having thus described the invention in general terms, reference will now be made to the accompanying drawings in which:

FIG. 6A is an enlarged vertical sectional view of a portion of FIG. 6;

DETAILED DESCRIPTION OF PREFERRED EMBODIMENTS

Figure 1:
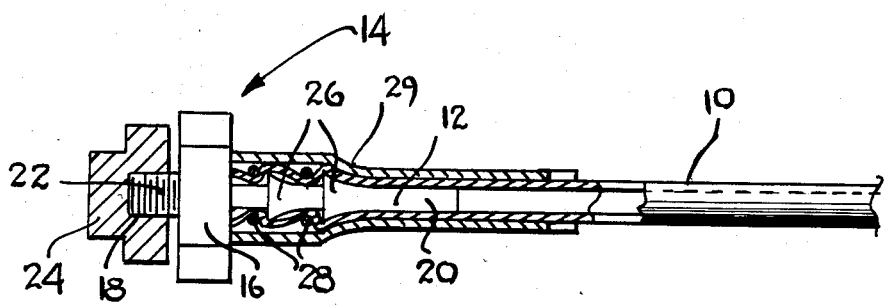
FIG. 1 is a side elevational view, partially broken away and in section, of a prior art catheter device showing the mounting of a flexible tube to a luer fitting.

Referring now in more detail and by reference characters to the drawings which illustrate preferred embodiments of the present invention, FIG. 1 illustrates a conventional prior art system for mounting a catheter tube 10 to a stem 12 of a luer fitting 14. The luer fitting 14 has an enlarged head 16 with an integrally formed outwardly opening port 18. This port 18 is in communication with an interior bore 20 through the stem 12 so as to communicate the bore 20 of the stem 12 with an external source of fluid.

The port 18 is provided with a central bore, not shown, in direct communication with the bore 20. Further, the bore 20 is integrally provided on its exterior surface with threads 22. A removable cap 24 is provided for removable and threaded disposition over the exterior threads 22 of the port 18 to open and close the latter.

The stem 12 is integrally provided with a plurality of longitudinally spaced apart, outwardly projecting cylindrically extending flanges or so-called "barbs" 26, in the manner as shown. These flanges 26 are tapered rearwardly, as shown, to facilitate insertion of the catheter tube 10 over the stem 12. In the regions between the barbs, a suture or similar thread 28 is tightly wrapped about the exterior surface of the catheter tube 10 to thereby obtain a seal between at least that portion of the catheter tube 10 and the stem 12 of the luer fitting.

This prior art assembly also included a sleeve 29 which extended over the portion of the catheter tube 10 on the stem 12, also in the manner as shown in FIG. 1.

Figure 2:
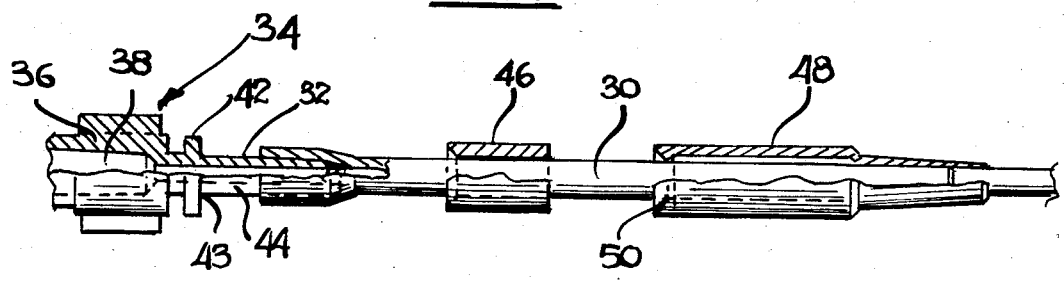
FIG. 2 is a side elevational view, partially broken away and in section, showing the assembly of the components used in the mounting of a flexible catheter tube to a luer fitting.
Figure 3:
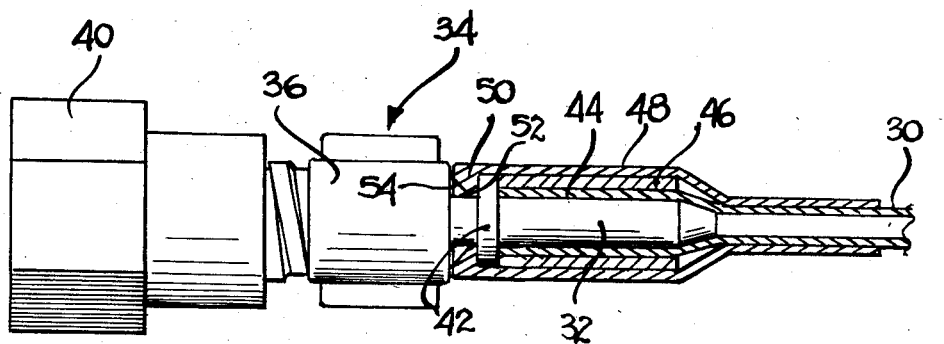
FIG. 3 is a side elevational view, partially in vertical section, of a catheter tube secured to the stem of a luer fitting.

One embodiment of the connector system A of the present invention is more fully illustrated in FIGS. 2 and 3 of the drawings. FIG. 2 illustrates the components in a position ready for assembly and FIG. 3 illustrates the position of the various components forming part of the system when in the fully assembled condition.

Referring again to FIGS. 2 and 3, a silicone rubber catheter tube 30 is provided for attachment to the stem 32 of a luer fitting 34 with a fluid tight seal therebetween. The luer 34 comprises an enlarged outer end or so-called "head" 36 which is provided with an inlet port 38 for communication with a central interior bore extending through the stem 32. Further, a removable cap 40 is provided for threadedly removable disposition over the port 38. In this way, a source of fluid can be connected to the luer fitting 34 for an intravenous introduction into a body through the luer fitting 34 and the catheter tube 30.

The luer fitting 34 is also provided, rearwardly of the enlarged head 36, reference being made to FIGS. 2 and 3, and on its stem portion 32 with an enlarged circumferentially extending shoulder 42 with a rearwardly facing wall 43. Further, by reference to FIGS. 2 and 3, it can be observed that the stem 32 has a relatively smooth continuous outer surface 44 and is uninterrupted from the shoulder 42 to the rearward end thereof. In addition, there are no substantial surface irregularities, such as flanges or barbs on the exterior surface thereof. The stem 32 is tapered at its rearward end to facilitate insertion of the catheter tube 30 over the stem 32.

It can also be observed that the interior surface of the catheter tube 30 is continuous and smooth. When the stem 30 is inserted into the catheter tube 30, the catheter tube 32 is pushed along the stem 32 until the forward end of the tube 30 engages the wall 43 of the outwardly flaring shoulder 42. Thereafter, a relatively rigid sleeve, as for example, a cylindrical sleeve 46, made from a fairly rigid polyethylene, polypropylene or the like, is disposed over that portion of the silicone rubber tube 30 on the stem 32. In this way, the relatively rigid sleeve 46 slightly compresses and forces the inner surface at the end of the silicone rubber tube firmly against the relatively smooth surface of the stem creating a fluid tight seal therebetween.

The end of the tube 30 abuts against a flat surface of the outwardly flaring shoulder 42 and an end of the sleeve 46 also abuts against the flat surface of the shoulder 42. Further, the annular surface of the shoulder 42 becomes contiguous with the annual surface of the sleeve 46 when in the abutted position.

The stem 32 of the fitting and for that matter the interior surface of the sleeve 46 are formed in such manner that there are no mold parting lines, since any parting lines could interfer with a fluid tight seal. Several known techniques for producing the parts without mold parting lines can be employed.

The fact that a relatively fluid tight seal has been achieved is surprising in view of the fact that it was always assumed that some means, such as a series of external flanges or ribs would be required in order to achieve the fluid tight seal. Otherwise it was always assumed that a means for wrapping about the portion of the rubber tube on the plastic stem, as for example, by means of thread, sutures or the like would be required to obtain a fluid tight seal. Nevertheless, Applicants have found that the relatively smooth surface finish on the stem, along with the relatively rigid sleeve are quite effective in obtaining this fluid tight seal, particularly in combination with a boot 48 hereinafter described.

Figure 4:
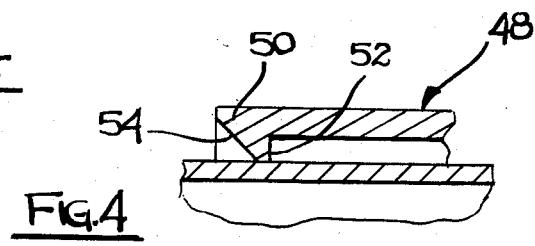
FIG. 4 is an enlarged vertical sectional view of a portion of the boot forming part of the assembly of FIGS. 2 and 3.

By further reference to FIGS. 2 and 3, it can be observed that a boot 48, also formed of a fairly flexible and bendable material, such as a silicone rubber, is disposed over the sleeve and the stem with the catheter tube on the stem. An in-turned flange 50 is integrally provided on the forward end of the cyclindrically shaped boot with a relatively flat rearwardly presented wall 52, reference being made to FIGS. 2, 3 and 4.

The flange is provided with a forward taper 44 to facilitate sliding over the sleeve 46. The forward end of the boot is adapted to extend over and engage the annular wall of the shoulder 42 and the in-turned flange 50 will engage the opposite annular face of the outwardly flaring shoulder 42. The in-turned flange 50 actually fills a substantial portion of the space between the sleeve 42 and the rearward face of the enlarged head 36. Further, the rearward end of the boot extends beyond the sleeve 46 and snuggly engages the exterior surface of the catheter tube 30.

The boot 48 further aids in the creation of a fluid tight seal between the stem 32 and the catheter tube 30 due to the fact that it fits snugly around the sleeve 46 and further biases the same into compressive engagement with the catheter tube 30 around the stem 32. In addition, the boot 48 also serves as a protective mechanism since it effectively extends over and provides an additional seal against the flange 42 and around a portion of the catheter tube 30, in the manner as shown in FIG. 3.

Figure 5:
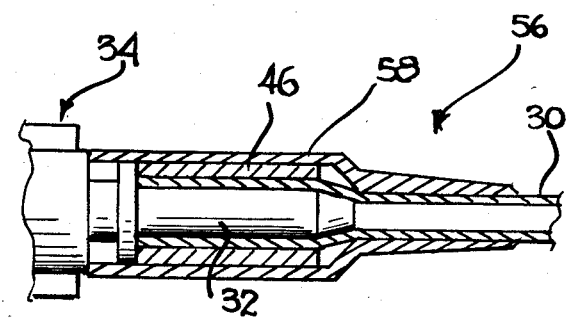
FIG. 5 is a vertical sectional view of a modified form of assembly for mounting a catheter tube to the stem of a luer fitting.

FIG. 5 illustrates another embodiment of a connector system 56 for connecting a catheter tube 30 to the stem 32 of a luer fitting 34. In this embodiment, like reference numerals represent components which are common to those components in the system of FIGS. 1–4. The method of connection of the catheter tube 30 to the fitting is similar to that previously described, except that there is a modified boot 58 which is provided in place of the boot 48 and which is adapted to engage the forwardmost end of the catheter tube 30 and the sleeve 46, also in the manner as shown in FIG. 5.

The boot 58 does not have an in-turned flange at its forward end but is relatively straight and is provided with a generally constant diameter at its forward end. The boot merely extends over and tightly engages the annular surface of the shoulder 42. The forward end of the boot engages the rearward face of the enlarged head 36 in the manner as shown.

Figure 6:
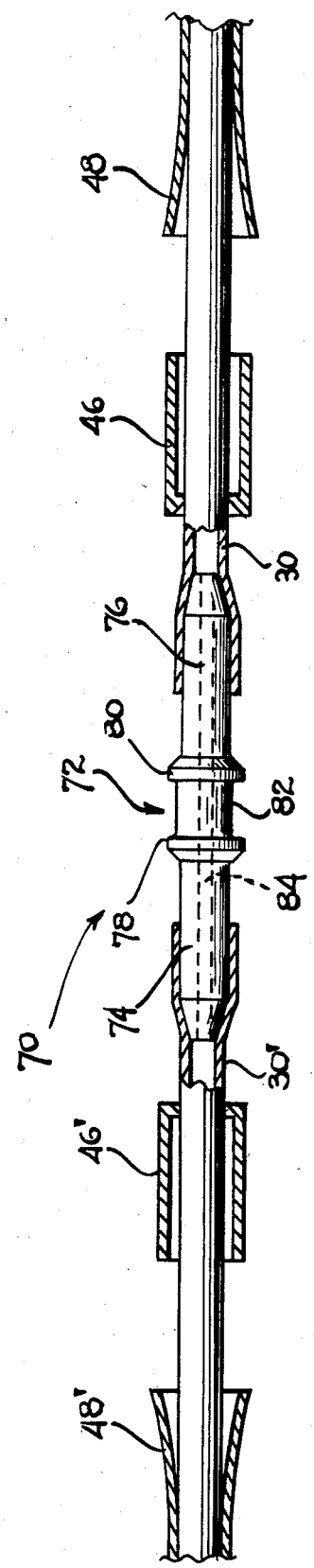
FIG. 6 is a vertical sectional view of another modified form of assembly for mounting a catheter tube to the stem of a luer fitting.

FIG. 6 illustrates still another modified assembly for securing the catheter tube 30 to the stem 32 of a fitting. This assembly is substantially identical to that illustrated in FIGS. 1-4 and comprises the inclusion of a silicone rubber adhesive 60 in the open portions where the inturned flange 50 extends into the annular recess between the shoulder 42 and the rearward face of the enlarged head 36. A similar adhesive 62 is introduced in the region at the rearward end of the sleeve 46 between the reducing portion of the boot 48 and the tube 30. These two regions of adhesive retentively hold the assembly together and further provided an additional sealing action.

Figure 7:
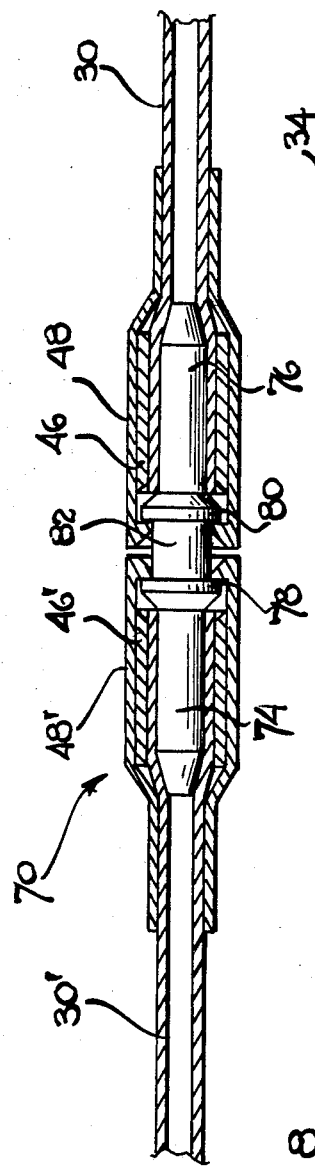
FIG. 7 is a vertical sectional view showing the mounting of a pair of catheter tubes to a repair fitting in accordance with the present invention.
Figure 8:
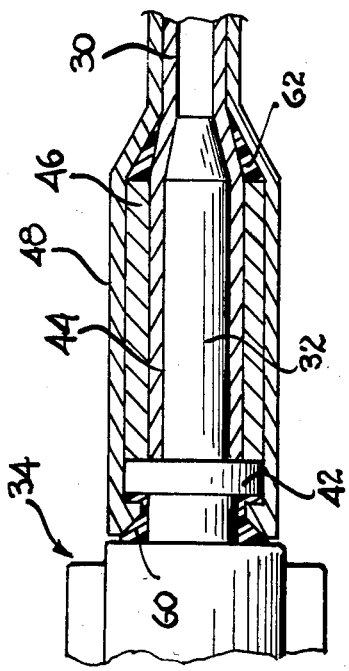
FIG. 8 is a vertical sectional view, similar to FIG. 7, and showing the completed assembly of the catheter tube to a repair fitting.

FIGS. 7 and 8 illustrate a further embodiment of a connector system 70 which is adapted as part of a repair kit for connecting one end of a catheter tube to another catheter tube or for connecting one tube section to another tube section. The connector system 70 of the invention comprises a fitting 72 having a pair of diametrically opposed outwardly extending stems 74 and 76. At their inner ends, each of the stems integrally merge into diametrially enlarged outwardly flaring circularly shaped abutment flanges 78 and 80, respectively. In addition, each of the stems 74 and 76 are integrally connected between the outwardly flaring flanges 78 and 80 by an extension tube 82. Each of the stems 74 and 76 and the connector tube 82 are all provided with an interior bore 84 permitting the passage of an intravenous fluid therein. The stem 76 is sized to receive a catheter tube 30 which is held in fluid tight engagement therewith by a sleeve 46 and which is also provided with a boot 48 so that there is a connection similar to that described in FIGS. 2, 3 and 4. FIG. 8 again shows the components in the assembled connected position.

The left-hand stem 74 is also sized to fit within another catheter tube 30' and which is also provided with a sleeve 46' capable of extending over the end of the catheter tube 30' when fitted on the stem 74. Finally, another boot 48' is similarly provided for extension over the sleeve 46' when in the assembled relationship. Here again, FIG. 8 illustrates the assembled relationship of the components in the connected position.

Figure 9:
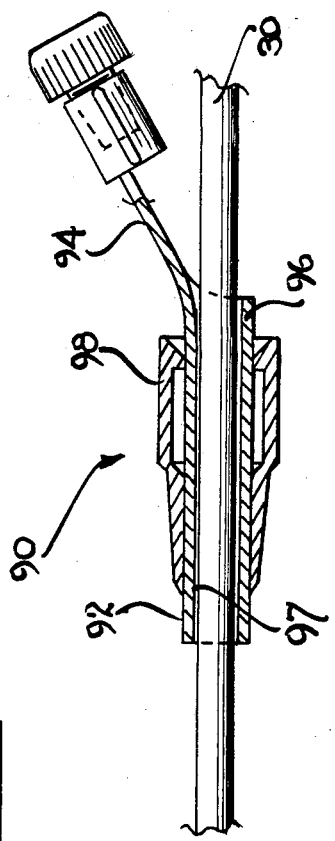
FIG. 9 is a side elevational view, partially broken away and in section, and showing the means for mounting a boot used in the catheter system of the present invention to a catheter tube.

Inasmuch as the boot 48, and for that matter the boot 48', are each comprised of a severed piece of catheter tube 30 which is stretched, some means must be provided to facilitate the concentric disposition of the boot over the catheter tube 30. The present invention provides a boot mounting device 90 which is more fully illustrated in FIG. 9 of the drawings. This boot mounting device 90 comprises a fairly rigid tube 92 which may be formed of a suitable plastic or other material and is provided at its right-end with a finger engagable tab 94 and which is somewhat flexible in its construction.

A severed length of catheter tube which functions as the boot 98 can be slightly expanded and slid onto the mounting tube 92. A so-called expanding dialator can be used for this purpose. In this way, the stretched catheter tube is fitted onto the mounting tube 92.

When it is desired to assemble the boot 98 onto a catheter tube, such as the catheter tube 30, a portion of this catheter tube is introduced into the interior bore 96 of the mounting tube 92, much in the manner as illustrated in FIG. 7. One portion of the boot 98 can be engaged and the mounting tube pulled from between the boot and the catheter tube 30 by the tab 94. In this way, the boot 98 will then be concentrically disposed about the catheter tube 30. When assembling the components to form a fluid tight seal between the catheter tube and a stem, the boot, once disposed upon the catheter tube, can be moved along and stretched about the assembly of the sleeve on the catheter tube over the stem.

Thus, there has been provided a relatively simple, but yet highly effective connector system for connecting a catheter tube to a luer fitting and also a connector system which enables repair of split catheter tubes without compromising the sterile environment of the catheter tube. In this respect, all components can be shipped in a sterile environment and assembled in a sterile field, as required.

The connector systems of the present invention are easy to manufacture and are relatively inexpensive. Further, inasmuch as there are no protrusions or irregular surfaces on the stems, it is quite easy for relatively inexperienced personnel to merely slide a catheter tube over the stem of the connector fittings. In addition, due to the smooth interior bore of the sleeve, it is also possible to easily extend the sleeve over the catheter tube when on the stem of the fittings. Finally, the same holds true in that the boot is readily moveable along the catheter tube to the assembled position as illustrated in the drawings.

Figure 10:
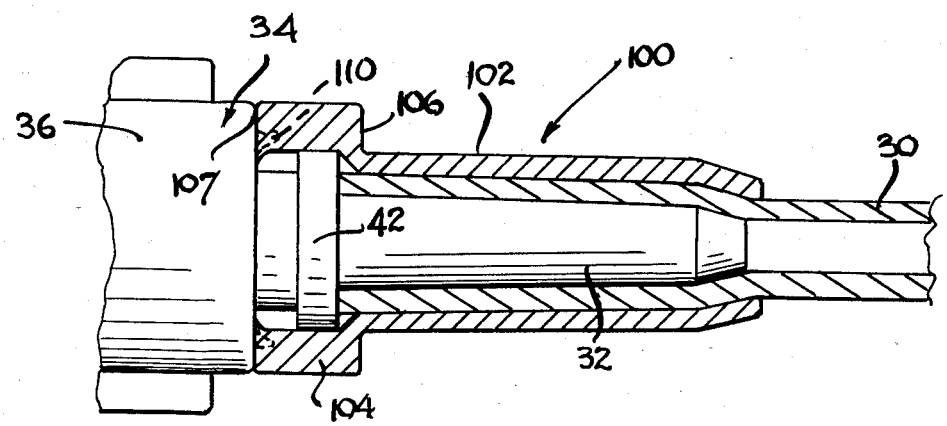
FIG. 10 is a vertical sectional view of still another modified assembly for mounting a catheter tube to the stem of a luer fitting.
Figure 11:
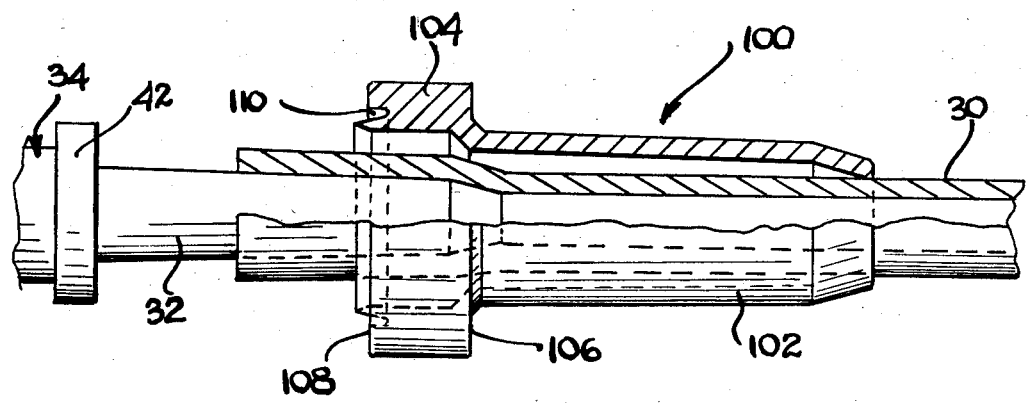
FIG. 11 is a vertical sectional view and showing the boot-sleeve combination used in the assembly of FIG. 10.

FIGS. 10 and 11 illustrate a modified arrangement of securing a catheter tube 30 to a luer fitting 34. In this case, the luer fitting is substantially similar to that previously described. This embodiment of the invention does not utilize an individual sleeve such as the sleeve 46 and an individual boot such as the boot 48. Rather, this embodiment of the invention utilizes a sleeve-boot combination 100 which is more fully illustrated in FIG. 11 of the drawings.

The sleeve-boot combination 100 generally comprises an elongate tubular section 102 which is adapted to fit over the catheter tube when the latter is disposed over the stem 32 of the luer fitting 34. The tubular section 102 integrally merges into an enlarged end section 104 which is adapted to extend over the enlarged flange 42 and engages the head 36. The enlarged end section 104 is provided with a relatively flat annularly extending outwardly facing wall 106 which is located and sized to receive the arm of an ultrasonic energy apparatus.

The sleeve-boot combination 100 is also preferably formed of a rigid polypropylene material much in the same manner as the sleeves which were previously described. However, the sleeve-boot combination 100 is capable of being sealed to the outwardly presented end wall of the luer fitting 34, as for example, by means of an ultrasonic seal 107.

Referring again to FIG. 11, it can be observed that the enlarged end section 104 is provided with a relatively flat annular wall 108 which faces the luer fitting 34. This wall is also provided with an annularly extending recess 110 which is located and sized to receive molten material which may flow from the end of the sleeve-boot combination 100 upon the application of energy, such as ultrasonic energy. Thus, when finally sealed, the sleeve-boot combination is rigidly adhered to the luer fitting 34. Moreover, the sleeve-boot combination also tightly fits over the enlarged flange 42 and also tightly engages the catheter tube 30 above the stem 32 of the luer fitting. In this way, a very efficient fluid tight seal is achieved. Furthermore, and due to the fact that the sleeve-boot combination 100 is sealed to the luer fitting 34, there is no inadvertent torsional force which could otherwise cause a separation or shearing of the catheter tube while on the luer fitting.

Thus there has been illustrated and described a unique and novel connector system for connecting a silicone rubber catheter tube to the stem of a fitting which may be a repair fitting or a luer fitting, in a highly efficient manner without utilization of sutures or protruberances on the stem of the fitting. Thus, the present invention fulfills all of the objects and advantages sought therefore. It should be understood that many changes, modifications, variations, and other uses and applications will become apparent to those skilled in the art after considering this specification and the accompanying drawings. Therefore, any and all such changes, modifications, variations, and other uses and applications which do not depart from the spirit and scope of the invention are deemed to be covered by the invention which is limited only by the following claims.

Having thus described my invention in general terms, what I desire to claim and secure by Letters Patent is:

1. A system for connecting a catheter tube to a fitting with a fluid tight seal, said system comprising:
   (a) a flexible and somewhat stretchable catheter tube having an outer wall with an interior bore and formed of a silicone rubber such that the wall is compressable to a substantially lesser thickness,
   (b) a plastic fitting formed of a thermoplastic material and having an elongate cylindrically shaped stem wherein the outer surface consists of a smooth outer surface with no substantial irregularities therein and sized to fit into the bore of the silicone rubber catheter tube in relatively fluid tight engagement therewith,
   (c) an enlarged shoulder on an end of said stem and adapted to be engaged by an end of the catheter tubing, said shoulder having a forward surface facing said tube and a rearward surface facing away from said tube,
   (d) a relatively rigid sleeve sized to fit over the portion of the catheter tube overlying the elongate stem and engaging the forward surface of said shoulder, said sleeve tightly engaging the exterior surface of the tube and compressing same against the stem to insure a relatively fluid tight seal between the fitting and tube and
   (e) a boot sized to extend over the relatively rigid sleeve and a portion of the tube not covered by said sleeve and to extend over said shoulder and engage the rearward surface of said shoulder.

2. The system of claim 1 further characterized in that the fitting is a luer fitting with a cap capable of being disposed over an end of the fitting opposite the stem.

3. The system of claim 1 further characterized in that the fitting also comprises a second elongate cylindrically shaped stem connected to and in fluid communication with the first named elongate cylindrically shaped stem and wherein the outer surface of the second stem consists of a smooth outer surface having no substantial irregulaties therein.

4. The system of claim 3 further characterized in that a second shoulder is located at the end of said second elongate stem and an extension integrally connects said two stems.

5. The system of claim 4 further characterized in that a second relatively rigid sleeve is sized to extend over a catheter tube on the second elongate stem and tightly engage the exterior surface of such tube and compress same against the second stem to insure another relatively tight fluid tight seal.

6. A connected catheter tube and fitting combination with a fluid tight seal therebetween, said combination comprising a plastic fitting formed of a thermoplastic material and having a first elongate cylindrically shaped stem wherein the outer surface consists of a smooth outer surface with no substantial irregularities therein, said plastic fitting also having a second elongate cylindrically shaped stem wherein the outer surface consists of a smooth outer surface having no substantial irregularities therein, said first stem being fitted into the bore of a first flexible somewhat stretchable silicone rubber catheter tube in relatively fluid tight engagement therewith, and which bore is formed by an annular wall which is substantially compressible, said second stem being fitted into the bore of a second flexible somewhat stretchable silicone rubber catheter tube in relatively fluid tight engagement therewith, and which bore of said second tube is formed by an annular wall which is substantially compressible, an enlarged first shoulder on an end of said first stem and the end of the first catheter tube engaging said first shoulder, a second shoulder on the end of said second elongate stem, and the end of the second catheter tube engaging said second shoulder, an intermediate extension connecting said first and second stems, a first relatively rigid sleeve extended over the portion of the first catheter tube on the first elongate stem and tightly engaging the exterior surface of the first tube and compressing same against the stem to insure a relatively tight fluid seal between the fitting and tube, and a relatively rigid second sleeve extended over the portion of the second catheter tube on the second elongate stem and tightly engaging the exterior surface of the second tube and compressing same against the second stem to insure another relatively tight fluid seal between the fitting and second tube.

7. The combination of claim 6 further characterized in that the fitting is a luer fitting with a cap capable of being disposed over an end of the fitting opposite the stem.

8. The combination of claim 6 further characterized in that a relatively rigid sleeve-boot combination which comprises said relatively rigid first sleeve sized to extend over the first catheter tube on the elongate stem and which is sealed resulting in a fluid flow of a portion of the sleeve-boot combination material with respect to the plastic fitting.

9. A method of connecting an end of a silicone tube to a fitting with a fluid tight seal therebetween, said method comprising:
   (a) inserting a silicone rubber boot over a portion of a flexible and somewhat stretchable silicone rubber catheter tube,
   (b) inserting a relatively rigid sleeve over a portion of the tube and closer to an end thereof than the boot,
   (c) inserting the cylindrically shaped elongate stem of a fitting, with the outer surface consisting of a smooth outer surface with no substantial irregularities therein, into the bore of a flexible and somewhat stretchable silicone rubber catheter tube,
   (d) pushing the end of the tube along said stem until the end is in engagement with an outwardly flaring shoulder at the end of the stem,
   (e) pushing the sleeve over the portion of the tube on the stem of the fitting until the sleeve abuts the shoulder on the fitting and tightly engages that portion of the tube and compresses same against the stem on the fitting, and (f) pushing the boot over the sleeve until one end of the boot engages the annular surface of the shoulder and extends beyond the shoulder and the boot extends over the entire sleeve and a portion of the tube beyond the sleeve.

10. The method of claim 9 further characterized in that said method comprises:

(a) inserting a second silicone rubber boot over a portion of a second flexible and somewhat stretchable silicone rubber catheter tube, (b) inserting a second relatively rigid sleeve over a portion of the tube closer to an end thereof than the second boot, (c) inserting a second cylindrically shaped elongate stem of said fitting with the outer surface consisting of a smooth outer surface with no substantial irregularities therein into the bore of the second flexible and somewhat stretchable silicone rubber catheter tube, (d) pushing the end of the second tube along said second stem until the end is in engagement with another outwardly flaring shoulder at the end of the second stem, (e) pushing the second sleeve over the portion of the second tube on the second stem of the fitting until the sleeve abuts the second shoulder on the fitting and tightly engages that portion of the second tube and compresses same against the second stem on the fitting, and (f) pushing the second boot over the second sleeve until one end of the second boot engages and extends over the second shoulder and the second boot extends over the entire second sleeve and a portion of the second tube beyond the second sleeve.

11. The method of claim 9 further characterized in that said boot is first introduced onto the exterior surface of a mounting tube and inserting one end of the catheter tube into the mounting tube and slipping the boot off of the mounting tube and onto the catheter tube.

12. The method of claim 11 further characterized in that a silicone adhesive is introduced in a region where the end of the boot extends over the shoulder.

13. A system for connecting a catheter tube to a fitting with a fluid tight seal, said system comprising:

(a) a flexible and somewhat stretchable catheter tube having an interior bore and formed of a silicone rubber, (b) a plastic fitting having an elongate cylindrically shaped stem wherein the outer surface consists of a smooth outer surface with no substantial irregularities therein and sized to fit into the bore of the silicone rubber catheter tube in relatively fluid tight engagement therewith, (c) an enlarged shoulder on an end of said stem and adapted to be engaged by an end of the catheter tube said shoulder having a forward surface facing said fitting and a rearward surface facing away from the fitting, (d) a relatively rigid sleeve sized to fit over the portion of the catheter tube overlying the elongate stem and tightly engage the exterior surface of the tube and compress same against the stem to insure a relatively fluid tight seal between the fitting and tube, said sleeve also engaging the forward surface of said shoulder and (e) a boot sized to extend over the relatively rigid sleeve and a portion of the tube not covered by said sleeve, said boot also capable of extending over and engaging said shoulder and the rearward surface of said shoulder.

14. A connected catheter tube and fitting combination with a fluid tight seal therebetween, said combination comprising a plastic fitting having an elongate cylindrically shaped stem wherein the outer surface consists of a smooth outer surface with no substantial irregularities therein, said stem being fitted into the bore of a flexible somewhat stretchable silicone rubber catheter tubing in relatively fluid tight engagement therewith, an enlarged shoulder on an end of said stem and the end of the catheter tube engaging said shoulder, said shoulder having a forward surface facing said fitting and a rearward surface facing away from said fitting, a relatively rigid sleeve extended over the portion of the catheter tube on the elongate stem and tightly engaging the exterior surface of the tube and compressing same against the stem to insure a relatively tight fluid seal between the fitting and tube, said sleeve also engaging the forward surface of said shoulder and a boot extended over the relatively rigid sleeve and a portion of the tube not covered by said sleeve, said boot also extending over and engaging said shoulder and the rearward surface of said shoulder.

* * * * *